United States Patent
Lee et al.

(10) Patent No.: US 12,115,088 B2
(45) Date of Patent: Oct. 15, 2024

(54) STENT AND METHOD FOR MANUFACTURING SAME

(71) Applicant: SEWOON MEDICAL CO., LTD., Cheonan-si (KR)

(72) Inventors: Jae Hee Lee, Seoul (KR); Mong Do Heo, Cheonan-si (KR); Sang-Chul Kim, Cheonan-si (KR)

(73) Assignee: SEWOON MEDICAL CO., LTD., Cheonan-si (KR)

( * ) Notice: Subject to any disclaimer, the term of this patent is extended or adjusted under 35 U.S.C. 154(b) by 292 days.

(21) Appl. No.: 17/373,786

(22) Filed: Jul. 13, 2021

(65) Prior Publication Data

US 2021/0361452 A1    Nov. 25, 2021

Related U.S. Application Data

(63) Continuation of application No. PCT/KR2019/003986, filed on Apr. 4, 2019.

(30) Foreign Application Priority Data

Jan. 28, 2019   (KR) .................. 10-2019-0010708

(51) Int. Cl.
   *A61F 2/90*     (2013.01)
   *A61F 2/07*     (2013.01)
   (Continued)

(52) U.S. Cl.
   CPC ............... *A61F 2/915* (2013.01); *A61F 2/07* (2013.01); *A61F 2/86* (2013.01); *A61F 2/90* (2013.01);
   (Continued)

(58) Field of Classification Search
   CPC ...... A61F 2/07; A61F 2/86; A61F 2/90; A61F 2250/0039
   See application file for complete search history.

(56) References Cited

U.S. PATENT DOCUMENTS

| | | | | |
|---|---|---|---|---|
| 2010/0256732 | A1* | 10/2010 | Shin | A61F 2/90 29/527.1 |
| 2013/0103162 | A1* | 4/2013 | Costello | A61F 2/90 118/500 |
| 2014/0277573 | A1* | 9/2014 | Gill | A61F 2/2476 623/23.68 |

FOREIGN PATENT DOCUMENTS

| | | |
|---|---|---|
| KR | 10-2001-0054677 A | 7/2001 |
| KR | 10-2009-0038209 A | 4/2009 |

(Continued)

OTHER PUBLICATIONS

KR-10-2013-0126779 with English translation (Year: 2013).*

*Primary Examiner* — Dinah Baria
(74) *Attorney, Agent, or Firm* — Nicholas Park

(57) ABSTRACT

A stent and a method for manufacturing the stent are disclosed. A stent according to an embodiment of the present invention is manufactured by using a jig having a cylindrical body on which a plurality of pins (P) are arranged in the circumferential direction (X) and the lengthwise direction (Y). The stent has a cylindrical structure, in which a wire member forms a zigzag pattern woven in the circumferential direction (X) with a predetermined width through the pins on the jig and a plurality of zigzag patterns formed in the circumferential direction (X), intersecting with one another, are arranged in the lengthwise direction with predetermined intervals (W) therebetween, forming a mesh structure with a rhombus pattern.

3 Claims, 9 Drawing Sheets

(51) Int. Cl.
*A61F 2/86* (2013.01)
*A61F 2/915* (2013.01)

(52) U.S. Cl.
CPC ............... *A61F 2002/91541* (2013.01); *A61F 2002/91575* (2013.01); *A61F 2220/0016* (2013.01); *A61F 2240/001* (2013.01); *A61F 2250/0039* (2013.01)

(56) References Cited

FOREIGN PATENT DOCUMENTS

| | | | |
|---|---|---|---|
| KR | 10-2010-0042478 | A | 4/2010 |
| KR | 10-2011-0088975 | A | 8/2011 |
| KR | 10-2013-0126776 | A | 11/2013 |

\* cited by examiner

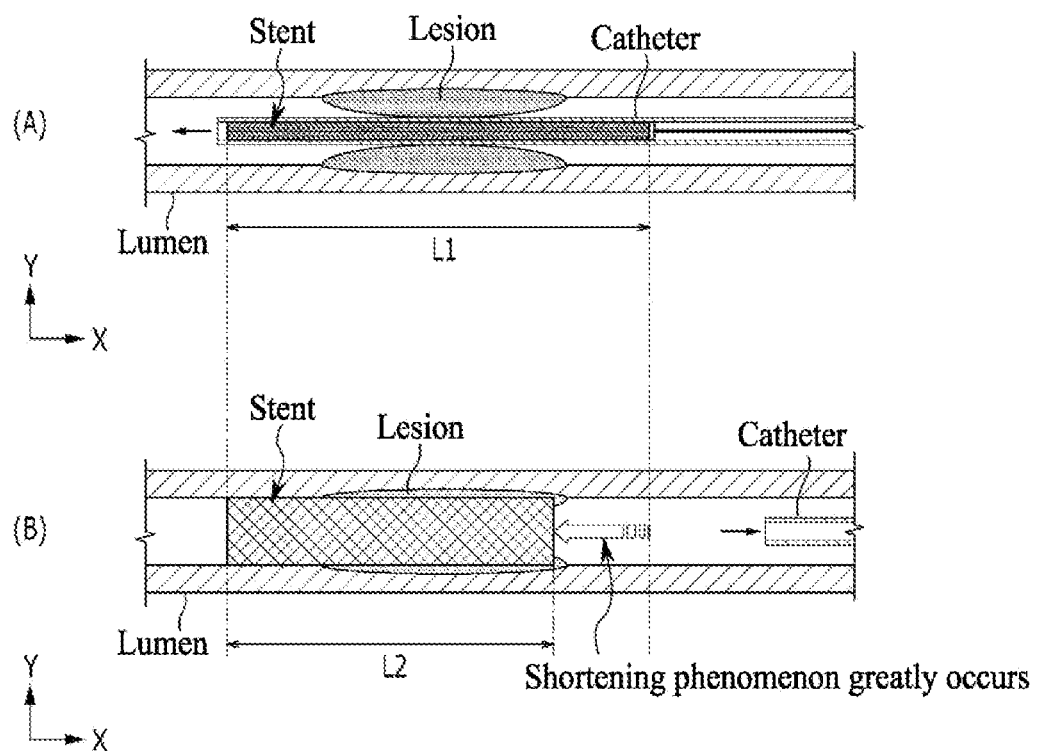
[Fig. 1]

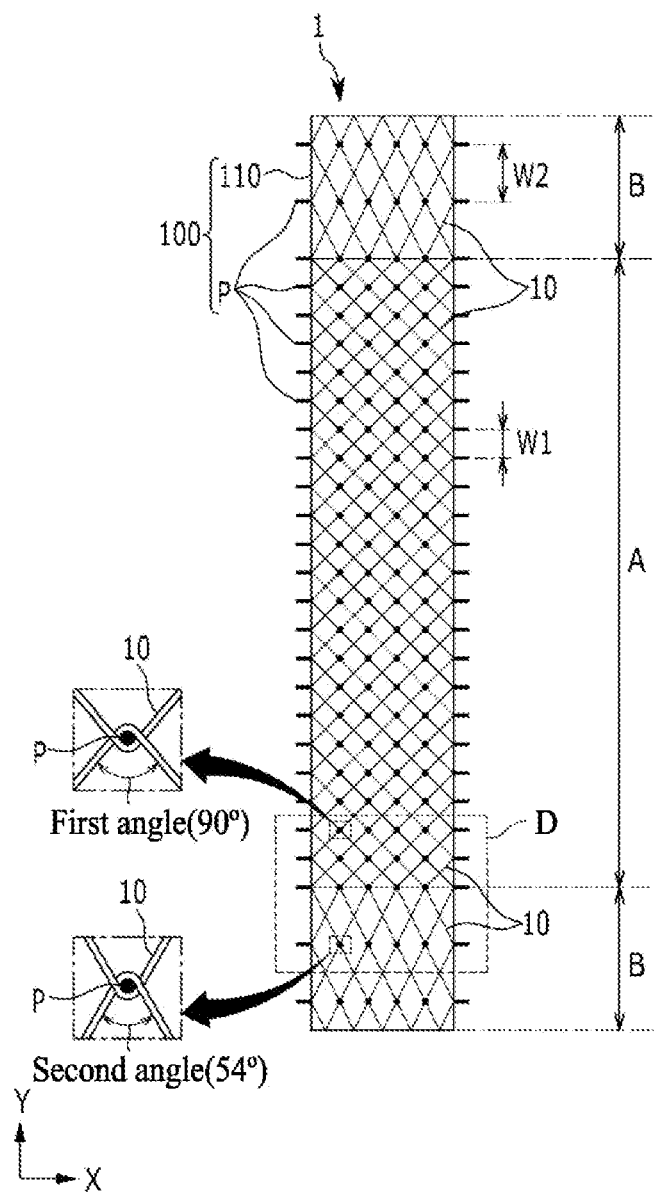
[Fig. 2]

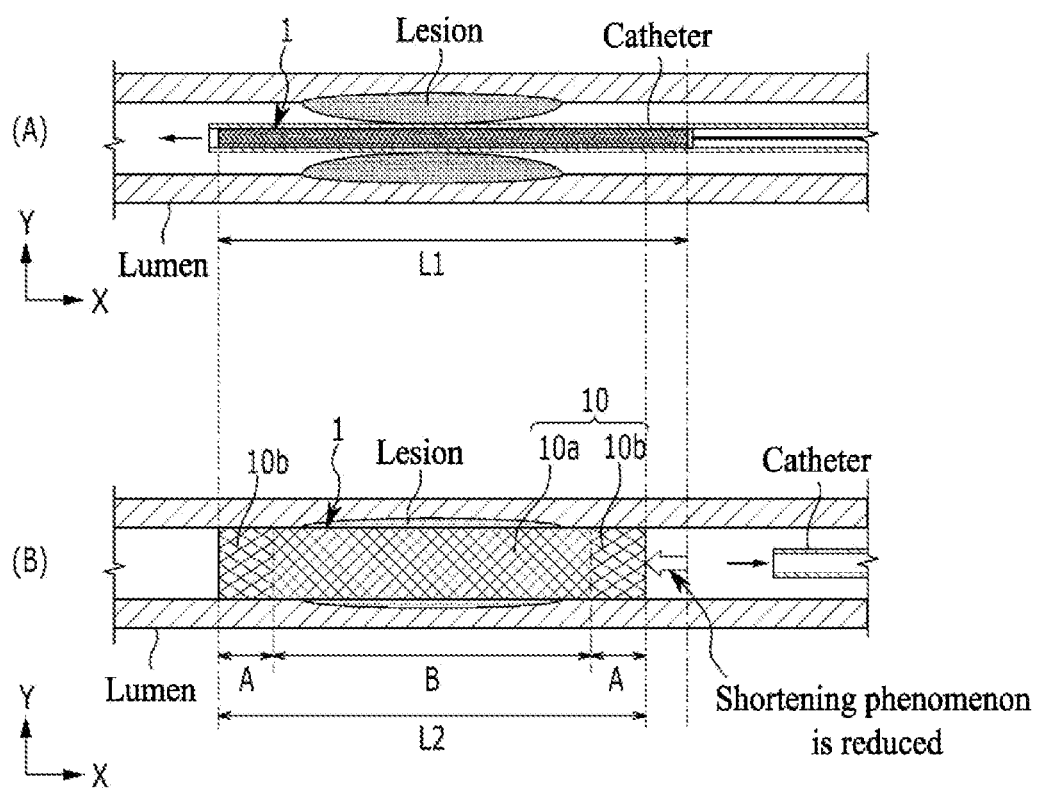
[Fig. 3]

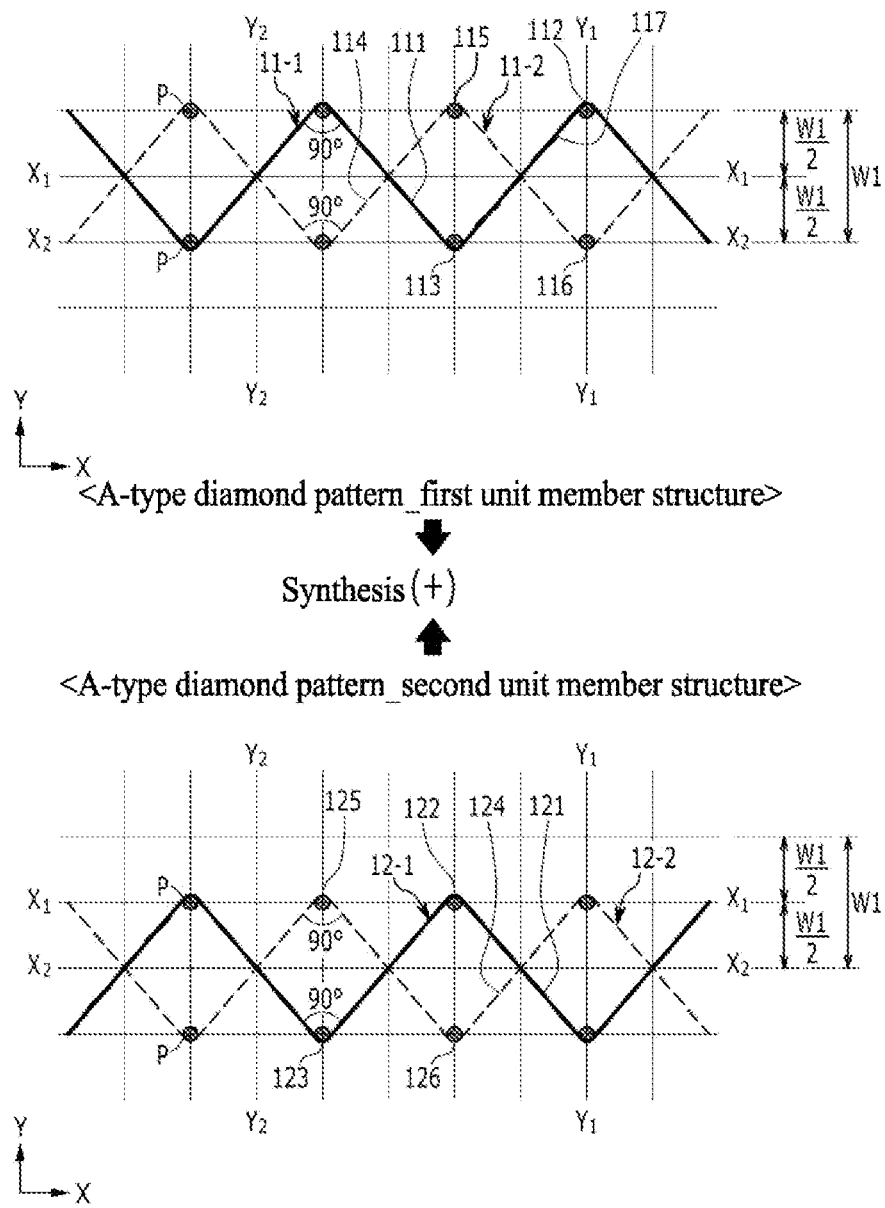
[Fig. 4]

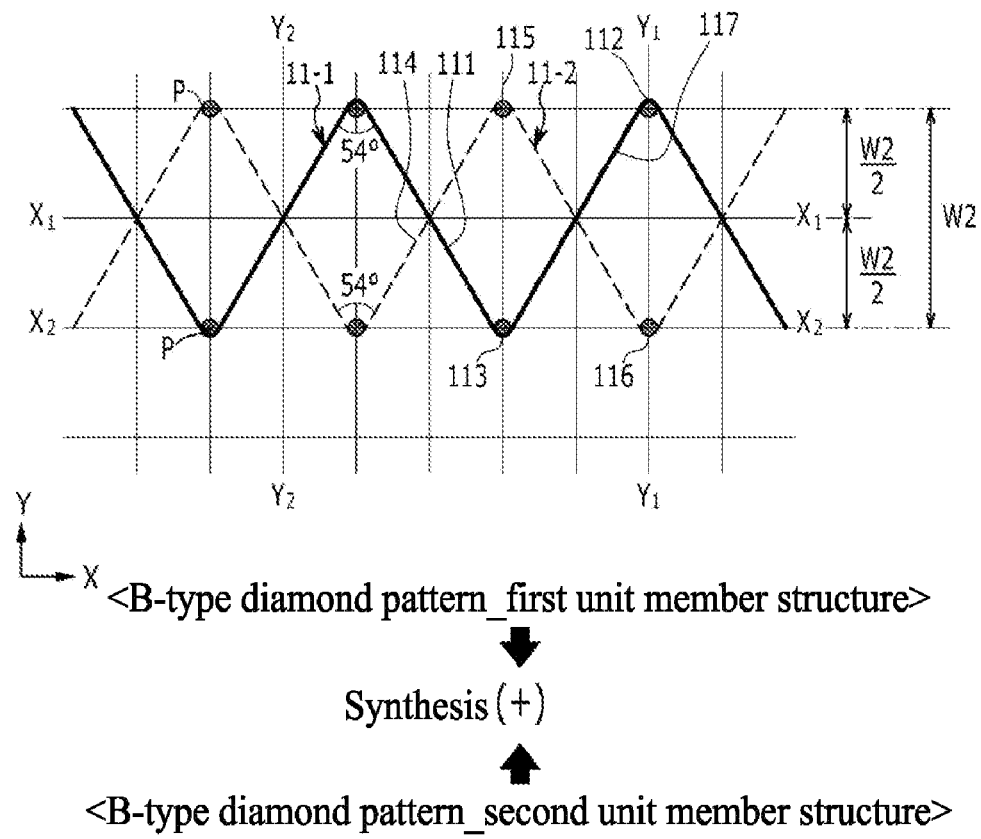
<B-type diamond pattern_first unit member structure>
↓
Synthesis (+)
↑
<B-type diamond pattern_second unit member structure>
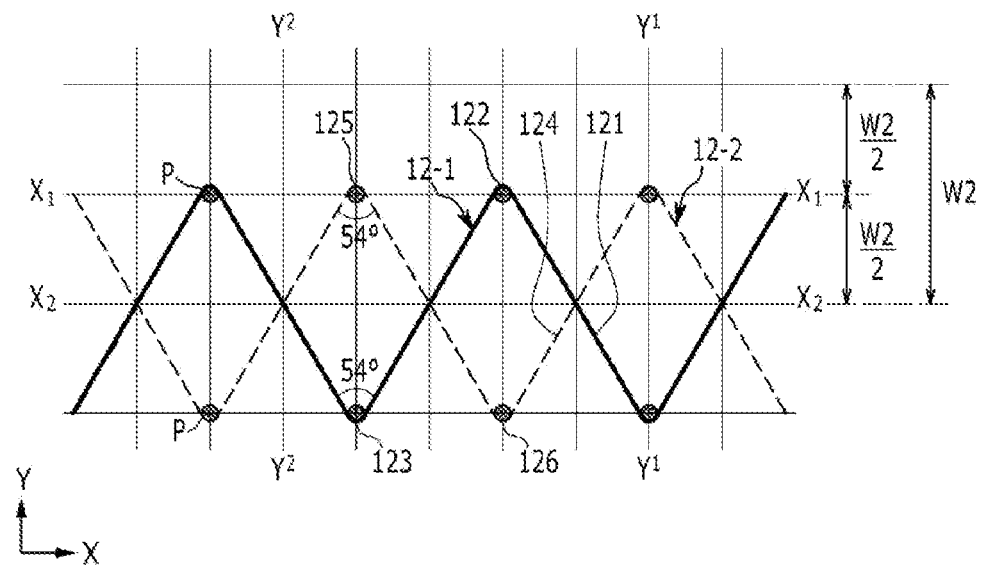
[Fig. 5]

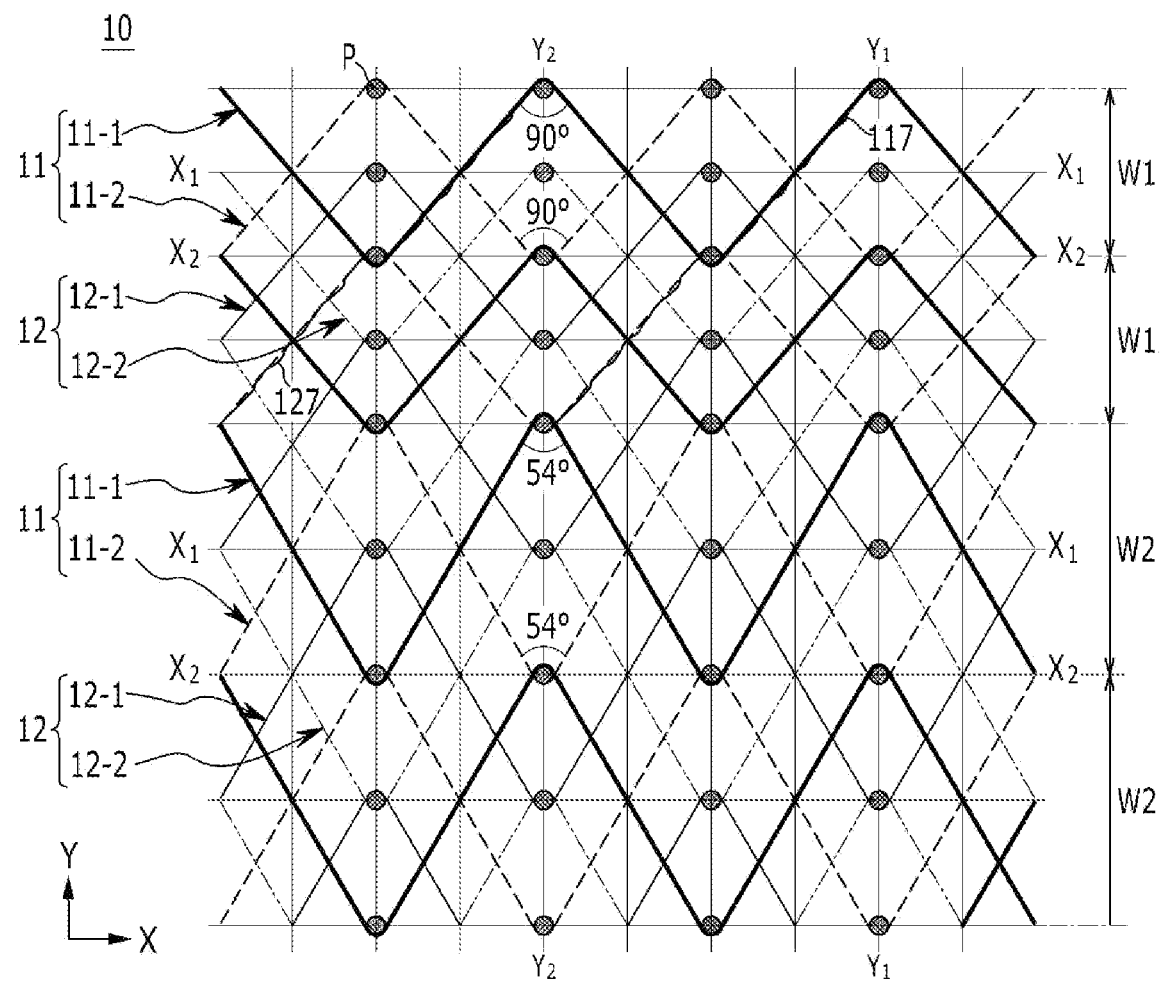
[Fig. 6]

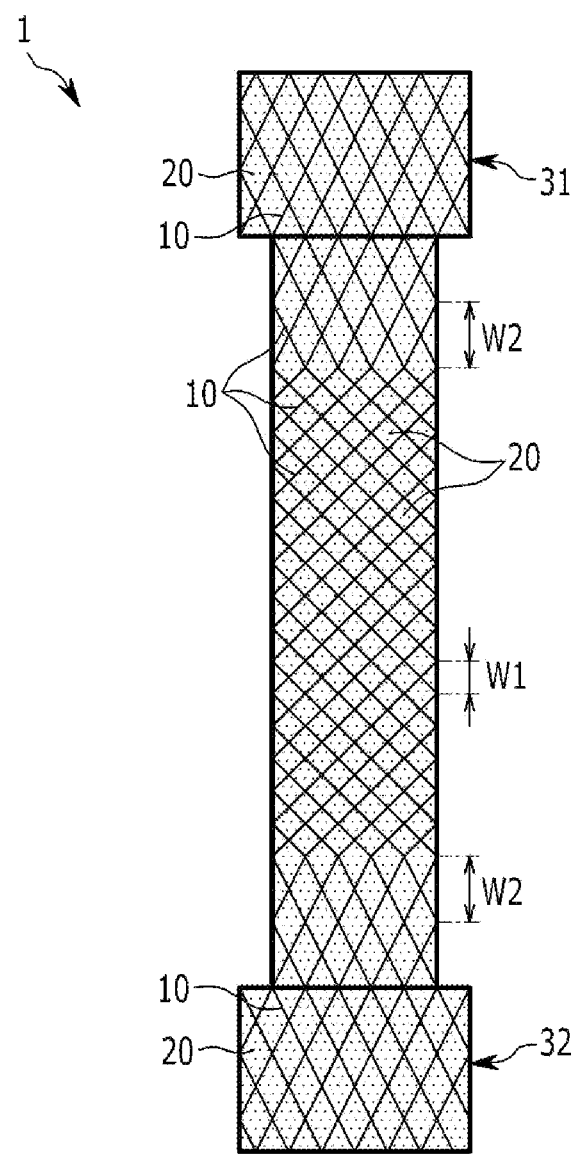
[Fig. 7]

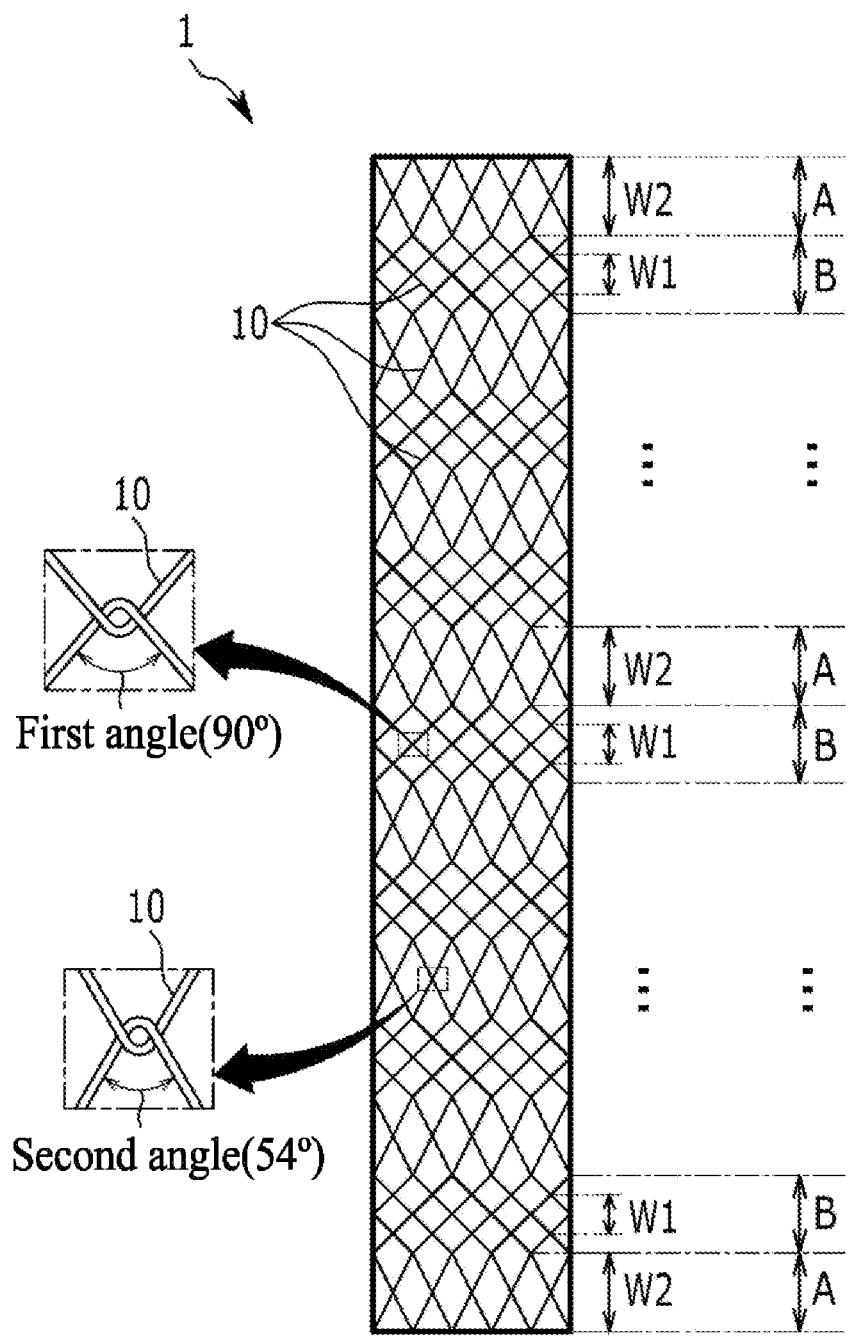
[Fig. 8]

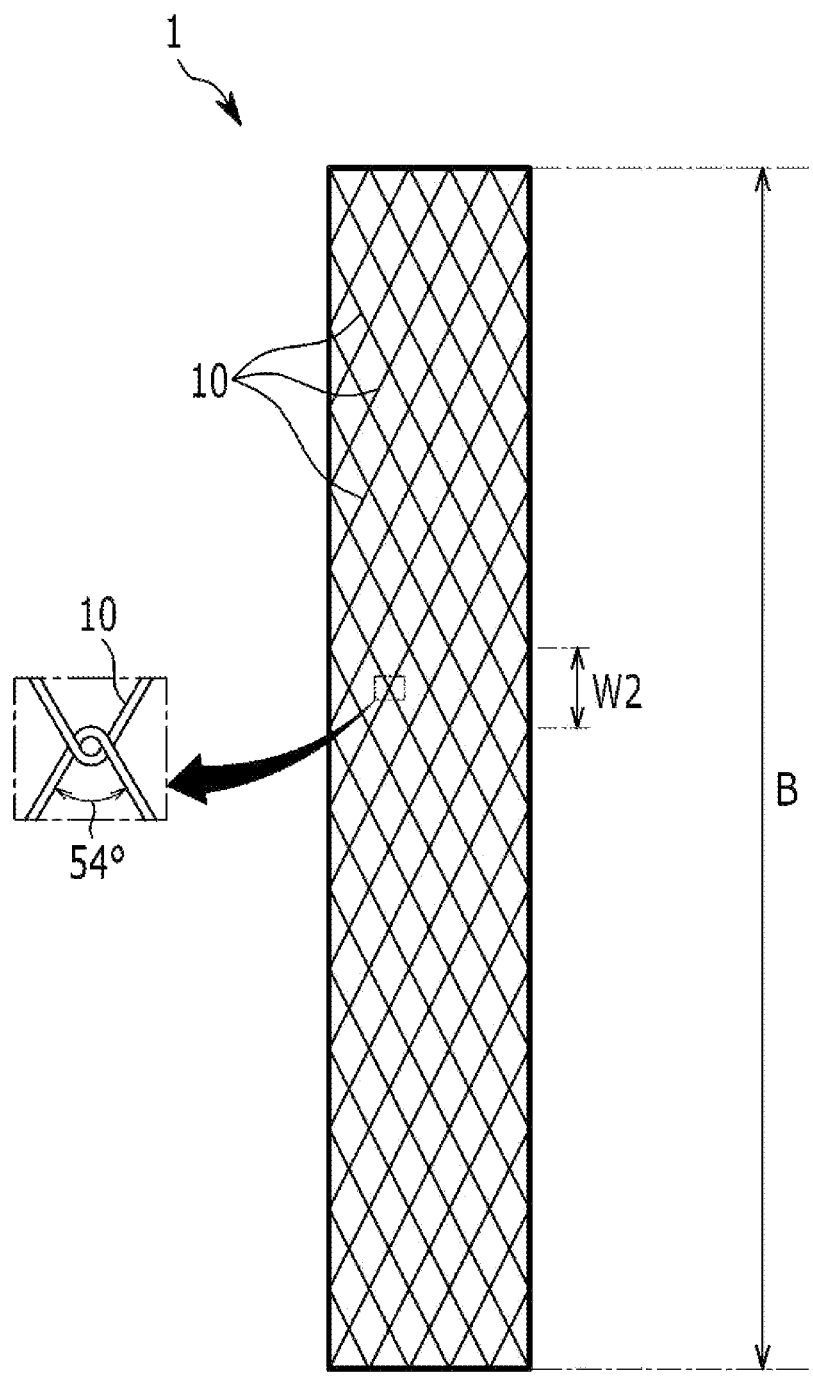
[Fig. 9]

STENT AND METHOD FOR MANUFACTURING SAME

CROSS-REFERENCE TO RELATED APPLICATION

This application is a US Bypass Continuation Application of International Application No. PCT/KR2019/003986, filed on Apr. 4, 2019 and designating the United States, the International Application claiming a priority date of Jan. 28, 2019, based on prior Korean Patent Application No. 10-2019-0010708, filed on Jan. 28, 2019. The disclosure of which is incorporated herein by reference in its entirety.

BACKGROUND

1. Field

The present invention relates to a stent and a method of manufacturing the stent, and more particularly, to a stent configured to minimize a shortening phenomenon in deployment in a lumen and a method of manufacturing the stent.

2. Related Art

Generally, when stenosis occurs in a lumen having a tubular structure such as an artery or an alimentary canal of a human body, food and drink or blood does not smoothly flow such that a function thereof is reduced and the reduction of function has a direct or indirect influence not only on diseases of the corresponding lumen but also the related circulatory system.

Accordingly, in medical institutions, when luminal stenosis is detected in a patient, a so-called stent procedure including inserting a stent into a lesion portion, expanding a stenosed passage, and maintaining an expanded state is performed.

Generally, a stent is a cylindrical mesh structure and has an autonomous elastic force so as to contract when an external force is applied and to expand when the external force is removed. In order to maintain the performance of the stent, it is necessary to satisfy features such as expandability for elastically expanding a lumen, adaptability for flexibly bending according to a bending shape of the lumen, and stability for not easily moving from an insertion position in the lumen, and the like. Accordingly, conventional stents are manufactured to have a dense mesh structure which has a large intersection angle formed in a longitudinal direction and a small intersection angle formed in a circumferential direction so as to secure an expansion force.

Here, recently, it is necessary to develop a stent with less of a shortening phenomenon in deployment in order to precisely seat the stent in a lesion portion in lumen in a stent procedure.

For example, FIG. 1 is an exemplary view for describing a problem caused by the occurrence of shortening in a conventional stent procedure.

(A) of FIG. 1 illustrates a state in which a stent loaded on a delivery catheter while being reduced in a diameter has been transferred to a lumen near a lesion portion in a stent procedure, (B) of FIG. 1 illustrates an example of an improperly performed procedure in which a stent deployed in the lumen does not properly cover a lesion portion due to a shortening phenomenon.

Here, the shortening phenomenon refers to a phenomenon in which a length L1 of a stent which elongates in a longitudinal direction Y when the stent is loaded on a catheter while being reduced in a diameter is shortened while expanding in a circumferential direction X due to its own elasticity when deployed in the lumen. Particularly, since the conventional stent is manufactured so that the intersection angle formed in the longitudinal direction Y is large and the intersection angle formed in the circumferential direction X is small to secure an expansion force, there are a problem in which the shortening phenomenon greatly occurs and a disadvantage of making the determination of a deployment position of the stent and the procedure difficult.

Also, once deployed, since the stent is not movable, when the stent is not properly installed in a stenosed portion, a function thereof may be reduced or stenosis may recur. In a serious case, there is a problem of performing the procedure again Items mentioned in the background art have been written to promote understanding of the background of the present invention and may include items which are not well-known to one of ordinary skill in the art.

SUMMARY

The present invention is directed to providing a stent manufactured in a structure configured to maintain an expansion force while minimizing a shortening phenomenon in deployment in a lumen after being loaded on a catheter to easily perform a stent procedure by a user and a method of manufacturing the stent.

One aspect of the present invention provides a stent manufactured using a jig, in which a plurality of pins (P) are arranged on a cylindrical body in a circumferential direction (X) and a longitudinal direction (Y), the stent including a cylindrical structure forming a mesh structure having a diamond pattern in which a zigzag pattern is formed by weaving a wire member in the circumferential direction (X) with a certain width using the pins (P) arranged on the jig and a plurality of such zigzag patterns formed in the circumferential direction (X) are arranged in a longitudinal direction of certain intervals (W) while intersecting with each other. Here, the cylindrical structure includes a double pattern in which a second intersection angle formed in the longitudinal direction (Y) of a B-type diamond pattern formed in both end portions is formed to be smaller than a first intersection angle formed in the longitudinal direction (Y) of an A-type diamond pattern formed in a central portion.

The wire member may include a first unit member and a second unit member formed to have unit lengths for the respective diamond patterns while lengths of the first unit member and the second unit member for forming the B-type diamond pattern may be formed to be longer than the A-type diamond pattern.

The first unit member may include a 1-1 turn formed by rotating once in a zigzag with a certain period on the basis of a certain reference point to form the cylindrical structure and a 1-2 turn formed by rotating once in a zigzag while correspondingly intersecting with the 1-1 turn with a phase difference therebetween and forming the mesh structure having the diamond pattern.

The second unit member may include a 2-1 turn formed by rotating once in a zigzag on the basis of a reference point which is a point at certain interval from a point facing a reference point of the 1-1 turn in a longitudinal direction while intersecting between the 1-1 turn and the 1-2 turn with a certain phase difference from the 1-1 turn to form a mesh structure and a 2-2 turn formed by rotating once in a zigzag while correspondingly intersecting with the 2-1 turn with a phase difference therebetween to form the mesh structure having the diamond pattern and uniformly intersecting between the 1-1 turn and the 1-2 turn to form the mesh structure.

The 1-1 turn and the 1-2 turn may respectively include 1-1 linear portions and 1-2 linear portions formed by a plurality of bending points and a plurality of 1-1 peak portions, a plurality of 1-2 peak portions, a plurality of 1-1 valley portions, and a plurality of 1-2 valley portions which connect the 1-1 linear portions and the 1-2 linear portion, respectively, while the 1-1 linear portions and the 1-2 linear portions intersect with each other so as to form a mesh.

The 2-1 turn and the 2-2 turn may respectively include 2-1 linear portions and 2-2 linear portions formed by a plurality of bending points and a plurality of 2-1 peak portions, a plurality of 2-2 peak portions, a plurality of 2-1 valley portions, and a plurality of 2-2 valley portions which connect the 2-1 linear portions and the 2-2 linear portion, respectively, while the 2-1 linear portions and the 2-2 linear portions intersect with each other so as to form the mesh structure having the diamond pattern and the 2-1 linear portions and the 2-2 linear portions intersect with the 1-1 linear portions and the 1-2 linear portions so as to form a mesh.

The first unit member may be connected by weaving one or more times along a 1-1 linear portion of the 1-1 turn after the 1-2 turn is formed and before the 2-1 turn is formed. Also, the second unit member may be connected by weaving one or more times along a 2-1 linear portion of the 2-1 turn after the 2-2 turn is formed and before the 1-1 turn next to the above 2-2 turn is formed.

1-1 and 1-2 peak portions and 1-1 and 1-2 valley portions of the 1-1 and 1-2 turns may be connected to 1-1 and 1-2 valley portions and 1-1 and 1-2 peak portions of next 1-1 and 1-2 turns next to the above 1-1 and 1-2 turns by holding each other. Also, 2-1 and 2-2 peak portions and 2-1 and 2-2 valley portions of the 2-1 and 2-2 turns may be connected to 2-1 and 2-2 valley portions and 2-1 and 2-2 peak portions of next 2-1 and 2-2 turns next to the above 2-1 and 2-2 turns by holding each other.

Angles of a peak portion and a valley portion which are formed in the B-type diamond pattern may be formed to be smaller than angles of a peak portion and a valley portion which are formed in the A-type diamond pattern.

The stent may further include a coating member applied to cover inner and outer surfaces of the cylindrical structure forming the mesh structure having the diamond pattern.

The stent may further include a movement preventing member extending from one end portion or both end portions of the cylindrical structure and having a diameter greater than that of the cylindrical structure.

Another aspect of the present invention provides a method of manufacturing a stent using a jig. The method includes a) forming a zigzag pattern by weaving, using the jig in which a plurality of pins (P) are perpendicularly arranged in a circumferential direction (X) and a longitudinal direction (Y) of a cylindrical body, a wire member in the circumferential direction (X) with a certain width and b) manufacturing a cylindrical stent having a mesh structure having a diamond pattern in which a plurality of such zigzag patterns formed in the circumferential direction (X) are arranged in a longitudinal direction of a certain interval (W) while intersecting with each other. Here, the plurality of pins (P) arranged on the jig are arranged at the same intervals along the circumferential direction (X) of the cylindrical body while second intervals W2 disposed in both end portions of a certain section are widely arranged in comparison to a first interval W1 disposed in a central portion of the certain section in the longitudinal direction (Y) of the cylindrical body (110).

Still another aspect of the present invention provides a stent manufactured using a jig, in which a plurality of pins (P) are arranged on a cylindrical body in a circumferential direction (X) and a longitudinal direction (Y). The stent includes a cylindrical structure forming a mesh structure having a diamond pattern in which a zigzag pattern is formed by weaving a wire member in the circumferential direction (X) with a certain width using the pins (P) arranged on the jig and a plurality of such zigzag patterns formed in the circumferential direction (X) are arranged in a longitudinal direction of certain intervals (W) while intersecting with each other. Here, in the cylindrical structure, an A-type diamond pattern having a first intersection angle relatively large in a longitudinal direction and a B-type diamond pattern having a second intersection angle relatively small in comparison to the A-type diamond pattern are repetitively formed with a certain section and period.

BRIEF DESCRIPTION OF THE FIGURES

The accompanying drawings used to explain example embodiments are only a portion of the example embodiments and other drawings may be obtained based on these drawings for those of ordinary skill in the art to which the disclosure pertains (hereinafter, "those skilled in the art") without an effort to reach the disclosure:

FIG. 1 is an exemplary view for describing a problem caused by the occurrence of shortening in a conventional stent procedure.

FIG. 2 illustrates a state in which a stent is manufactured using a jig according to a first embodiment of the present invention.

FIG. 3 is a conceptual view for describing an effect of reducing a shortening phenomenon while the stent manufactured using the jig according to the first embodiment of the present invention is utilized in a procedure.

FIG. 4 is a development view illustrating a structure of the stent according to the first embodiment of the present invention in which a first unit member and a second unit member have been rotated twice in an A-type diamond pattern corresponding to a central portion A.

FIG. 5 is a development view illustrating a structure of the stent according to the first embodiment of the present invention in which a first unit member and a second unit member have been rotated twice in a B-type diamond pattern corresponding to both end portions B.

FIG. 6 is a development view illustrating an enlarged region "D" of FIG. 2 according to the first embodiment and illustrates a part where an A-type diamond pattern structure and a B-type diamond pattern structure are connected.

FIG. 7 illustrates components of a stent according to a second embodiment of the present invention.

FIG. 8 illustrates a mesh structure of a stent according to a third embodiment of the present invention.

FIG. 9 illustrates a mesh structure of a stent according to a fourth embodiment of the present invention.

DETAILED DESCRIPTION

Hereinafter, embodiments of the present invention will be described in detail with reference to the attached drawings so as to be implemented by one of ordinary skill in the art. However, the present invention may be implemented to have a variety of different forms and is not limited to the embodiments described herein. Throughout the drawings, for clear description of the present invention, irrelevant parts will be omitted. Throughout the specification, like elements will be referred to with like reference numerals.

Throughout the specification, when a portion is stated as "including" a component, unless defined particularly otherwise, it means that the portion may not exclude another component but may further include another component. Also, the terms such as " . . . portion," " . . . module," and the like disclosed herein refer to a unit configured to perform at least one function or operation and may be implemented as hardware, software, or a combination thereof.

Throughout the specification, the terms such as first, second, and the like may be used to describe a variety of components, and the components are not limited to the terms. The terms are used only for distinguishing one component from another. For example, a first component may be referred to as a second component, and similarly, the second component may be referred to as the first component without departing from the scope of the concept of the present disclosure.

Hereafter, a stent and a method of manufacturing the stent according to an embodiment of the present invention will be described in detail with reference to the drawings.

FIG. 2 illustrates a state in which a stent is manufactured using a jig according to a first embodiment of the present invention.

Referring to FIG. 2, a stent 1 according to an embodiment of the present invention is manufactured as a cylindrical structure having a mesh structure formed, using a jig 100 including a plurality of pins P perpendicularly arranged in a circumferential direction X and a longitudinal direction Y of a cylindrical body 110, by weaving a wire member 10 in the circumferential direction X with a certain width to form zigzag patterns in the circumferential direction X and arranged in a longitudinal direction at certain intervals W while intervening with each other.

The mesh structure has a shape in which diamond patterns including four sides having the same length are arranged in the circumferential direction X and the longitudinal direction Y of the stent 1.

Here, as described above in a description of the background of the present invention, a conventional stent is manufactured to have a large intersection angle formed in the longitudinal direction Y and a small intersection angle formed in the circumferential direction X to secure an expansion force such that there is a problem in which a shortening phenomenon greatly occurs in deployment. However, on the other hand, when a stent is manufactured to have a small intersection angle formed in the longitudinal direction Y and a large intersection angle formed in the circumferential direction X, a shortening phenomenon of the stent may be reduced but there is a problem in which there is a trade-off relationship in which the expansion force of the stent is reduced.

Accordingly, the jig 100 according to the first embodiment of the present invention is characterized by including the pins P arranged at the same intervals in the circumferential direction X of the cylindrical body 110 while second intervals W2 arranged in both end portions B are larger than first intervals W1 arranged in the central portion A in the longitudinal direction Y of the cylindrical body 110.

The stent 1 according to the first embodiment of the present invention which is manufactured using the jig 100 having the above features has features in which intersection angles formed longitudinally in the central portion A and both end portions B are differently formed and a second intersection angle formed in the both end portions B is formed to be smaller than a first intersection angle formed in the central portion A.

For example, since the first intersection angle formed in a diamond pattern of the central portion A (hereinafter, referred to as "A-type diamond pattern") in the longitudinal direction Y is formed to be 90 degrees, the stent 1 secures an expansion force corresponding to a lesion portion. Also, since the second intersection angle formed in a diamond pattern of both end portions B (hereinafter, referred to as "B-type diamond pattern") in the longitudinal direction Y is formed to be small, i.e., 54 degrees, a shortening phenomenon may be reduced. Hereinafter, although the first intersection angle will be assumed to be 90 degrees and the second intersection angle is assumed to be 54 degrees to assist understanding of description, the present invention is not limited thereto.

Accordingly, as shown in FIG. 2, the stent 1 may include the wire member 10 formed to have a double pattern including a section A in the central portion including the A-type diamond pattern and a section B in both end portions including the B-type diamond pattern.

Meanwhile, FIG. 3 is a conceptual view illustrating an effect of reducing a shortening phenomenon while the stent manufactured using the jig according to the first embodiment of the present invention is utilized in treatment procedure.

Referring to FIG. 3, a lesion portion of a stenosed lumen generally requires a large expansion force and a front end portion and a rear end portion thereof do not require a relatively large expansion force in comparison to the lesion portion. Also, in the stent procedure, the central portion A may be deployed to be seated in the lesion portion in the longitudinal direction Y of the stent.

Accordingly, since the intersection angle of both end portions B, which does not require a large expansion force, in the longitudinal direction Y is formed to be smaller than that of the central portion A while the intersection angle of the central portion A which requires a large expansion force is formed to be greater than that of the both end portions B, the stent 1 according to the first embodiment of the present invention may maximally reduce a shortening phenomenon while securing an expansion force for restoring the stenosed lumen.

Accordingly, the stent 1 according to the embodiment of the present invention provides effects of facilitating a surgical operation and securing an expansion force by reducing the shortening phenomenon using the double patterns manufactured to have different intersection angles along the longitudinal direction so as to restore an original shape of the lesion portion.

Meanwhile, the structure of the stent 1 described above will be described below in more detail with reference to the drawings.

FIG. 4 is a development view illustrating the structure of the stent according to the first embodiment of the present invention in which a first unit member and a second unit member have been rotated twice in the A-type diamond pattern corresponding to the central portion A.

FIG. 5 is a development view illustrating the structure of the stent according to the first embodiment of the present invention in which the first unit member and the second unit member have been rotated twice in the B-type diamond pattern corresponding to both end portions B.

FIG. 6 is a development view illustrating an enlarged region "D" of FIG. 2 according to the first embodiment and illustrates a part where an A-type diamond pattern structure and a B-type diamond pattern structure are connected.

Referring to FIGS. 4 to 6, the stent 1 according to the first embodiment of the present invention includes a first unit member 11 and a second unit member 12 capable of self-contracting and expanding and having flexibility and unit lengths. Here, a perpendicular intersection point on a checkerboard shape is a position of a hole H in which the pin P is inserted and installed on the jig 100, and a round spot at the intersection point means a state in which the pin P is installed in the hole H. While the pins P are disposed in the jig 100, the first unit member 11 and the second unit member 12 are woven using the following method so that the cylindrical stent 1 is manufactured.

First, referring to FIGS. 4 to 6, the first unit members 11 formed in the central portion of the stent 1 are arranged at certain intervals along a reference circumferential surface with a certain width in the circumferential direction X so as to form a cylindrical structure and rotate once in a zigzag with a certain period on the basis of certain reference points X1-X1 and Y1-Y1 so as to form a 1-1 turn 11-1.

Also, after the 1-1 turn 11-1 is formed, the first unit members 11 rotate once in a zigzag while mutually and correspondingly intersecting with a bending point of the 1-1 turn 11-1 and forming a mesh structure with a phase difference from the 1-1 turn 11-1 so as to form a 1-2 turn 11-2.

The second unit members 12 formed in the central portion of the stent 1 are arranged at certain intervals with a certain width in the circumferential direction X along the same circumferential surface as that of the first unit member 11 so as to form a cylindrical structure. Also, with points at a certain distance in the longitudinal direction Y from points facing the reference points of the 1-1 turn 11-1 becoming the reference points X1-X1 and Y1-Y1 and a certain phase difference from the 1-1 turn 11-1, the second unit members 12 uniformly intersect with each other between the 1-1 turn 11-1 and the 1-2 turn 11-2 so as to form a mesh structure and form a 2-1 turn 12-1 by rotating once in a zigzag.

After the 2-1 turn 12-1 is formed, the second unit members 12 are correspondingly intersecting with bending points of the 2-1 turn 12-1 with a phase difference from the 2-1 turn 12-1 so as to form a mesh structure, uniformly intersect with each other between the 1-1 turn 11-1 and the 1-2 turn 11-2, and rotate once in a zigzag while forming a mesh structure so as to form a 2-2 turn 12-2.

The 1-1 turn 11-1 and the 1-2 turn 11-2 and the 2-1 turn 12-1 and the 2-2 turn 12-2 may be formed to have the same width along a central line (X1-X1) or (X2-X2) having uniform width differences W1/2 to flexibly adapt to a bending shape of the lumen and to have the same period with a certain phase difference.

The 1-1 turn 11-1 includes 1-1 linear portions 111 formed in a zigzag by a plurality of bending points and a plurality of 1-1 peak portions 112 and a plurality of 1-1 valley portions 113 which connect the 1-1 linear portions 111.

Also, the 1-2 turn 11-2 includes 1-2 linear portions 114 formed in a zigzag by a plurality of bending points and configured to form a mesh by intersecting with the 1-1 linear portions 111 and 1-2 peak portions 115 and 1-2 valley portions 116 which connect the 1-2 linear portions 114 and are formed to correspond to the 1-1 valley portions 113 and 1-1 peak portions 112.

The 2-1 turn 12-1 includes 2-1 linear portions 121 formed in a zigzag by a plurality of bending points and configured to form a mesh by intersecting with the 1-1 linear portions 111 and 1-2 linear portions 114 and a plurality of 2-1 peak portions 122 and a plurality of 2-1 valley portions 123 which connect the 2-1 linear portions 121.

Also, the 2-2 turn 12-2 includes 2-2 linear portions 124 formed in zigzags by a plurality of bending points and configured to form a mesh by intersecting with the 1-1 linear portions 111, the 1-2 linear portions 114 and the 2-1 linear portions 121 and 2-2 peak portions 125 and 2-2 valley portions 126 which connect the 2-2 linear portions 124 and are formed to correspond to the 2-1 valley portions 123 and the 2-1 peak portions 122.

As described above, there is formed an intersection angle (for example, 90 degrees) between the peak portion and the valley portion which are formed in the longitudinal direction Y of the A-type diamond pattern formed by combining (+) the first unit member 11 and the second unit member 12 which are each formed in a zigzag in the central portion A of the stent 1. This is a greater value than that (for example, 54 degrees) between the peak portion and the valley portion which are formed in the longitudinal direction Y of the B-type diamond pattern of both end portions B which will be described below and allows an expansion force to be secured with respect to the lesion portion where the lumen is stenosed.

Meanwhile, after the 1-2 turn 11-2 is formed and before the 2-1 turn 12-1 is formed, the first unit member 11 may previously form first connection portions 117 connected by weaving at least one time along the 1-1 linear portions 111 of the 1-1 turn 11-1 as shown in FIG. 6.

Also, after the 2-2 turn 12-2 is formed and before the 1-1 turn 11-1 next to the 2-2 turn 12-2 is formed, the second unit member 12 may previously form second connection portions 127 connected by weaving at least one time along the 2-1 linear portions 121 of the 2-1 turn 12-1.

Meanwhile, the 1-1 peak portion 112 and the 1-1 valley portion 113 of the 1-1 turn 11-1 are connected to the 1-1 valley portion 113 and the 1-1 peak portion 112 of the next 1-1 turn 11-1 correspondingly next to the above 1-1 turn 11-1 by holding each other as shown in FIG. 6. Also, the 1-2 peak portion 115 and the 1-2 valley portion 116 of the 1-2 turn 11-2 are connected to the 1-2 valley portion 116 and the 1-2 peak portion 115 of the next 1-2 turn 11-2 correspondingly next to the above 1-2 turn 11-2 by holding each other.

Also, the 2-1 peak portion 122 and the 2-1 valley portion 123 of the 2-1 turn 12-1 are connected to the 2-1 valley portion 123 and the 2-1 peak portion 122 of the next 2-1 turn 12-1 correspondingly next to the above 2-1 turn 12-1 by holding each other. Also, the 2-2 peak portion 125 and the 2-2 valley portion 126 of the 2-2 turn 12-2 are connected to the 2-2 valley portion 126 and the 2-2 peak portion 125 of the next 2-2 turn 12-2 correspondingly next to the above 2-2 turn 12-2 by holding each other.

The first unit member 11 and the second unit member 12 may be formed of a shape memory alloy such as nitinol and the like so as to allow a uniform expansion force to be applied when a temperature is constant like the lumen. Also, it is obvious that materials of the first unit member 11 and the second unit member 12 are not limited thereto, and in addition thereto, well-known materials or novel materials may be generally applied to manufacturing of the stent.

Accordingly, the stent 1 according to the embodiment of the present invention is formed by allowing the 1-1 turn 11-1 and the 1-2 turn 11-2 and the 2-1 turn 12-1 and the 2-2 turn 12-2 rotate once in a zigzag to intersect and interfere with each other therebetween with uniform width differences and phase differences. Also, the 1-1 linear portions 111 and the 1-2 linear portions 114 intersect with the 2-1 linear portions 121 and the 2-2 linear portions 124 so as to form a mesh structure.

Accordingly, respective gaps between the 1-1 turn 11-1 and the 1-2 turn 11-2 and the 2-1 turn 12-1 and the 2-2 turn 12-2 may be densely manufactured to be a very small size and easily worked while reducing a manufacturing time.

Also, the 1-1 peak portion 112, the 1-2 peak portion 115, the 1-1 valley portion 113, and the 1-2 valley portion 116 are connected to the 1-1 valley portion 113, the 1-2 valley portion 116, the 1-1 peak portion 112, and the 1-2 peak portion 115 which are next to the 1-1 turn 11-1 and the 1-2 turn 11-2 by holding each other as shown in FIG. 6.

Also, in the first unit members 11, the 1-2 turn 11-2 is formed and then connected by weaving one or more times along the 1-1 linear portion 111 of the 1-1 turn 11-1. In the second unit member 12, the 2-2 turn 12-2 is formed and then connected by weaving one or more times along the 2-1 linear portion 121 of the 2-1 turn 12-1.

Accordingly, the stent 1 may be inserted into the stenosed portion of a lumen and form a path in the lumen while being prevented from being bent with a certain curvature and maintaining its own shape, that is, the cylindrical shape as it is even when the lumen is severely bent in a variety of shapes.

Subsequently, referring to FIGS. 5 and 6, since a configuration and a method of the B-type diamond pattern applied to both end portions B of the stent 1 according to the embodiment of the present invention are similar to those of the A-type diamond pattern of the central portion A of the stent described with reference to FIGS. 4 and 6, a repetitive description thereof will be omitted.

However, the B-type diamond pattern formed in both end portions B of the stent 1 has a feature in which an intersection angle between the peak portion and the valley portion formed according to an interval between the pins P widely arranged in the longitudinal direction Y of the jig 100 is manufactured to be smaller than the A-type diamond pattern of the central portion A of the stent shown in FIG. 4.

Accordingly, since the B-type diamond pattern formed in both end portions B of the stent 1 is less deformed while the stent 1 is loaded on a catheter or deployed in the catheter in comparison to the A-type diamond pattern formed in the central portion A, there is provided an effect of minimizing a shortening phenomenon.

Also, since movement of a portion where the stent 1 and the organ (lumen) come into contact with each other is minimized, movement of the stent 1 caused by the movement of the organ is reduced so that there is an effect of preventing the lesion portion from being damaged due to the movement of the stent.

As described above, according to the embodiment of the present invention, since a stent includes a mesh structure having double patterns in which an A-type diamond pattern formed in a central portion along a longitudinal direction of the stent has a relatively greater intersection angle and a B-type diamond pattern formed in both end portions has a relatively small intersection angle, there are effects of reducing a shortening phenomenon and securing an expansion force for a particular portion corresponding to a lesion portion.

Also, since the stent 1 may be flexibly bent according to a bending shape of a lumen without distortion while a partial expansion force may be significantly improved at a bent portion and may not easily move from an insertion position of the lumen, a path of a stenosed portion at the bent portion is reliably formed so that there is an effect in which blood, food and drink, or the like may smoothly flow.

Meanwhile, although the embodiment of the embodiment of the present invention has been described above, the present invention is not limited to the embodiment and a variety of modifications are possible. Accordingly, the embodiment is defined as [First Embodiment] and an additional modifiable embodiment will be continuously described.

Second Embodiment

FIG. 7 illustrates components of a stent according to a second embodiment of the present invention.

Referring to FIG. 7, the first embodiment may be equally applied to the stent 1 according to the second embodiment of the present invention and there is a difference therebetween in which a coating member 20 and movement preventing members 31 and 32 are additionally applied thereto. Accordingly, hereinafter, a repetitive description will be omitted and the additional components will be mainly described.

The stent 1 is coated with the coating member 20 such as polyurethane or the like to cover inner and outer surfaces of the stent 1 so as to minimize friction with the lumen while being inserted into the lesion portion of the lumen and expanding therein and to allow blood, food and drink, or the like to smoothly flow.

The coating member 20 may be applied by coating the outer surface of the stent 1 while being heated at a certain temperature. Also, the stent 1 may be dipped into a tank in which the coating member 20 is melted and taken out and then cooled to be coated.

Also, the stent 1 may further include the movement preventing members 31 and 32 extending from any one end portion or both end portions and having a greater diameter than a diameter of the stent 1.

The movement preventing members 31 and 32 support the stent 1 inserted into the lesion portion from the lumen and prevent the stent from arbitrarily moving in the lumen.

The movement preventing members 31 and 32 may preferably be configured in the same manner as the B-type diamond pattern formed in both end portions B of the stent 1 so as to minimize a shortening phenomenon. However, a structure of the movement preventing members 31 and 32 is not limited thereto and may include a structure in which a unit member is wound spirally or in a zigzag or the like in addition to the A-type diamond pattern.

Also, inner and outer surfaces of the movement preventing members 31 and 32 may be coated with the coating member 20 to be integrally connected with the stent 1.

Also, the movement preventing members 31 and 32 may be formed to have the same center as the stent 1 so as to be easily contractible or expandable when being inserted into a stenosed portion of the lumen.

According to the second embodiment of the present invention, the stent may be coated with the coating member so as to provide an effect of allowing blood, food and drink, or the like to smoothly flow while preventing blood, food and drink, or the like from flowing into another organ.

Third Embodiment

Meanwhile, FIG. 8 illustrates a mesh structure of a stent according to a third embodiment of the present invention.

Referring to FIG. 8, a stent 1 according to a third embodiment of the present invention is similar to the above-described embodiments and has a difference of having a mesh structure in which the A-type diamond pattern and the B-type diamond pattern are repeated with a certain section and period along the entire longitudinal direction Y. That is, the stent 1 has a shape in which the section A in which the A-type diamond pattern is formed and the section B in which the B-type diamond pattern is formed are repeated without distinction between the central portion and both end portions of the above embodiment in the entire longitudinal direction Y. Here, the certain intervals and periods are not limited to FIG. 8 and may be manufactured in a structure modified according to a layout design of the pins P of the jig 100.

Accordingly, the stent 1 according to the embodiment of the present invention has effects of reducing a shortening phenomenon in the entire longitudinal direction Y and securing expandability in the circumferential direction X.

Fourth Embodiment

Meanwhile, FIG. 9 illustrates a mesh structure of a stent according to a fourth embodiment of the present invention.

Referring to FIG. 9, a stent 1 according to a fourth embodiment of the present invention is similar to the above-described embodiments and has a difference of having a mesh structure in which the B-type diamond patterns continue along the entire longitudinal direction Y. This provides an effect of having a mesh structure configured to reduce a shortening phenomenon of the stent 1 to the most optimized state. Also, as described with reference to FIGS. 4 to 6, since the stent 1 includes a dense pattern formed by mutually combining and weaving a primary turn and a secondary turn in which the first unit member 11 and the second unit member 12 which are capable of self-contracting and expanding and formed to have flexibility and a unit length are formed in a zigzag, an expansion force thereof may be maintained.

According to embodiments of the present invention, since a stent includes a mesh structure having double patterns in which an A-type diamond pattern formed in a central portion along a longitudinal direction of the stent has a relatively large intersection angle and a B-type diamond pattern formed in both end portions has a relatively small intersection angle, there are effects of reducing a shortening phenomenon and securing an expansion force for a particular portion corresponding to a lesion portion.

Since movement of the stent in a longitudinal direction is reduced so that movement of the stent installed in an organ (lumen) is reduced and movement of a part where the stent and the organ come into contact with each other is also minimized, movement of the stent caused by movement of the organ is reduced so that there is an effect of preventing damage of a lesion portion caused thereby.

Also, since the stent 1 can be flexibly bent according to a bending shape of lumen without distortion while a partial expansion force can be improved at a bent portion and cannot easily move from an insertion position of the lumen, a path of a stenosed portion at the bent portion is reliably formed so that there is an effect in which blood, food and drink, or the like can smoothly flow.

Although the embodiments of the present invention have been described above in detail, the scope of the present invention is not limited thereto and includes a variety of modifications made by those skilled in the art using the basic concept of the present invention defined by the following claims.

What is claimed is:

1. A stent, inserted into a lesion portion of a stenosed lumen for smooth flow of blood comprising a cylindrical structure forming a mesh structure of a plurality of diamond shaped cells,
    wherein the mesh structure comprises A-type diamond patterns, longitudinally adjacent to B-type diamond patterns,
    wherein each diamond shaped cell of the A-type diamond patterns has a first width, in a circumferential direction of the cylindrical structure, and the each diamond shaped cell of B-type diamond patterns has a second width, in the circumferential direction of the cylindrical structure, wherein the first width and the second width are equal,
    wherein each diamond shaped cell of the A-type diamond patterns has a first length, in a longitudinal direction of the cylindrical structure, and each diamond shaped cell of the B-type diamond patterns has a second length, in the longitudinal direction of the cylindrical structure, wherein the second length is larger than the first length to reduce a shortening phenomenon of the stent,
    wherein each diamond shaped cell of the A-type diamond patterns has a first intersection angle at each of a peak and a valley in the longitudinal direction, and each diamond shaped cell of the B-type diamond patterns has a second intersection angle at each of a peak and a valley in the longitudinal direction, and
    wherein the first intersection angle is 90 degrees, and the second intersection angle is 54 degrees.

2. The stent of claim 1, further comprising a coating member applied to cover inner and outer surfaces of the cylindrical structure forming the mesh structure having the diamond patterns.

3. The stent according to claim 1, further comprising a movement preventing member extending from one end portion or both end portions of the cylindrical structure and having a diameter greater than that of the cylindrical structure.

* * * * *